US00PP12669P2

(12) United States Plant Patent
Noodelijk

(10) Patent No.: US PP12,669 P2
(45) Date of Patent: Jun. 4, 2002

(54) CHRYSANTHEMUM PLANT NAMED 'EVEREST SALMON'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/276,693

(22) Filed: Mar. 26, 1999

(51) Int. Cl.[7] ..... A01H 5/00
(52) U.S. Cl. ..... Plt./297
(58) Field of Search ..... Plt./297, 286

*Primary Examiner*—Bruce R. Campell
*Assistant Examiner*—June Hwu

(57) ABSTRACT

A chrysanthemum plant named 'Everest Salmon' characterized by its medium sized blooms with salmon ray-florets and yellow-green disc florets.

2 Drawing Sheets

RELATED APPLICATIONS

The present application is related to the following co-pending applications:

| Application Ser. No. | Filing Date | Title |
|---|---|---|
| 09/276,695 | March 26, 1999 | 'Everest Pink' |
| 09/276,633 | March 26, 1999 | 'Everest White' |

BACKGROUND OF THE INVENTION

'Everest Salmon' is a product of a breeding and selection program that had the objective of finding color mutants of 'Everest Pink'. The new plant of the present invention comprises a new and distinct cultivar of chrysanthemum plant that is a natural occuring sport of a parent chrysanthemum named 'Everest Pink' (Ser. No. 09/276,695). A comparison with parent chrysanthemum 'Everest Pink' is also made in this application. The new cultivar was discovered as a whole plant mutation in May 1996 by Rob Noodelijk in a controlled environment (greenhouse) in Rijsenhout, Holland. The first act of asexual reproduction of 'Everest Salmon' was accomplished when vegetative cuttings were taken from the initial selection in September 1996 in Rijsenhout, Holland.

SUMMARY OF THE INVENTION

The present invention is a new and distinct variety of chrysanthemum bearing medium sized blooms with salmon ray-florets and yellow-green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
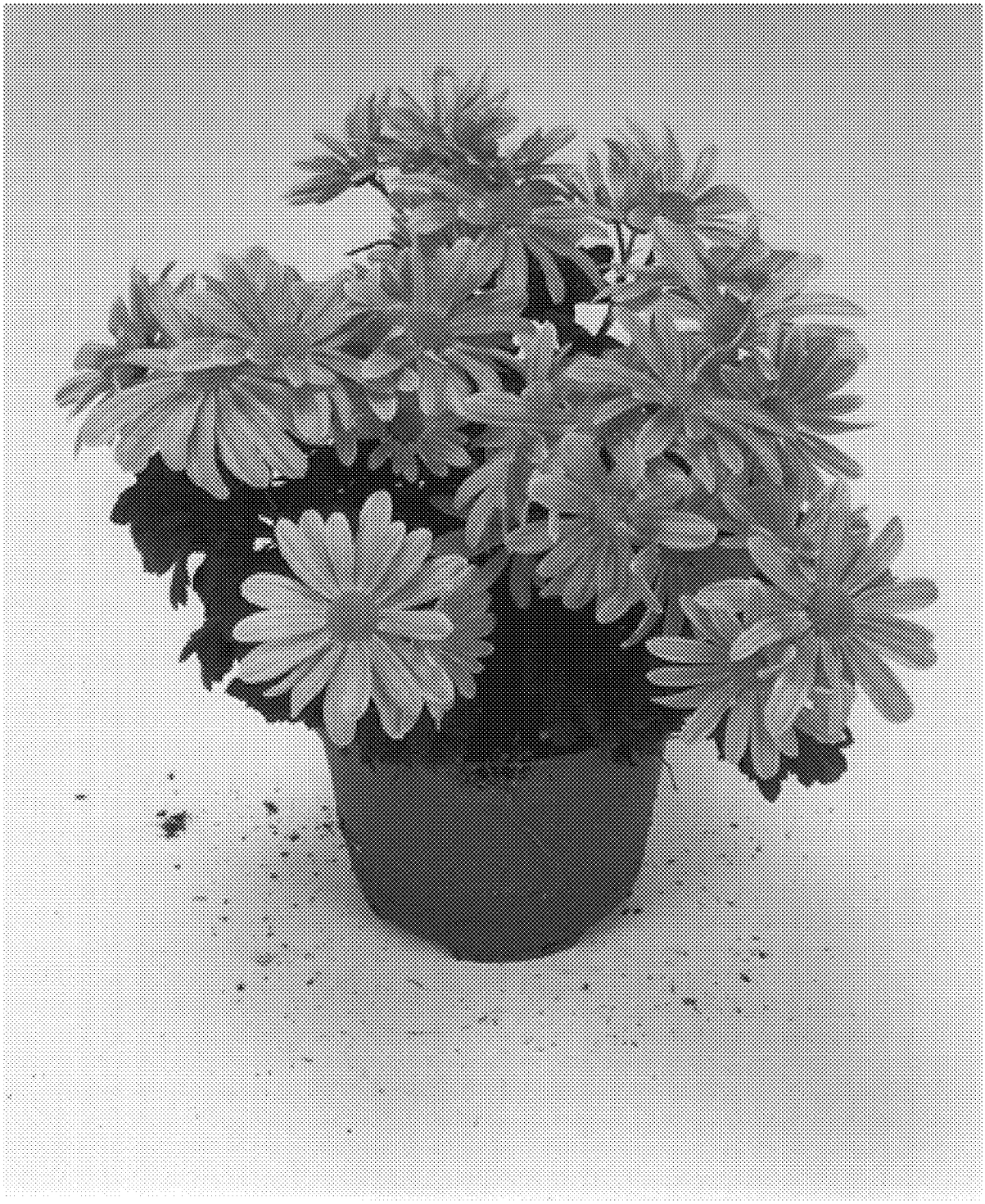
FIG. 1 shows a plant of the cultivar in full bloom.
Figure 2:
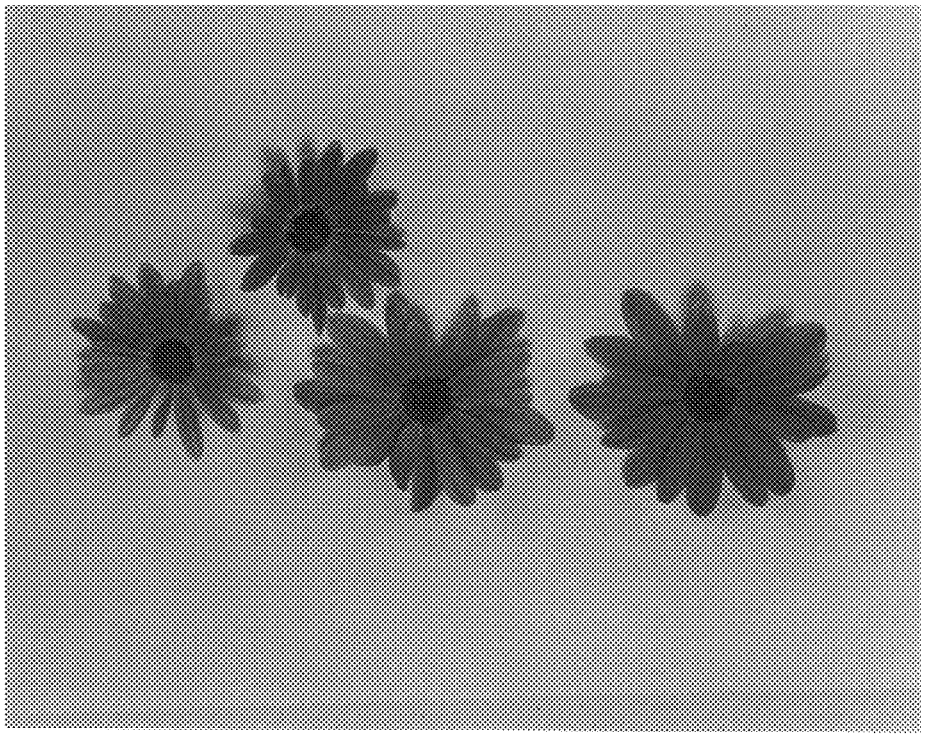
FIG. 2 shows the various stages of bloom of the new cultivar.
Figure 3:
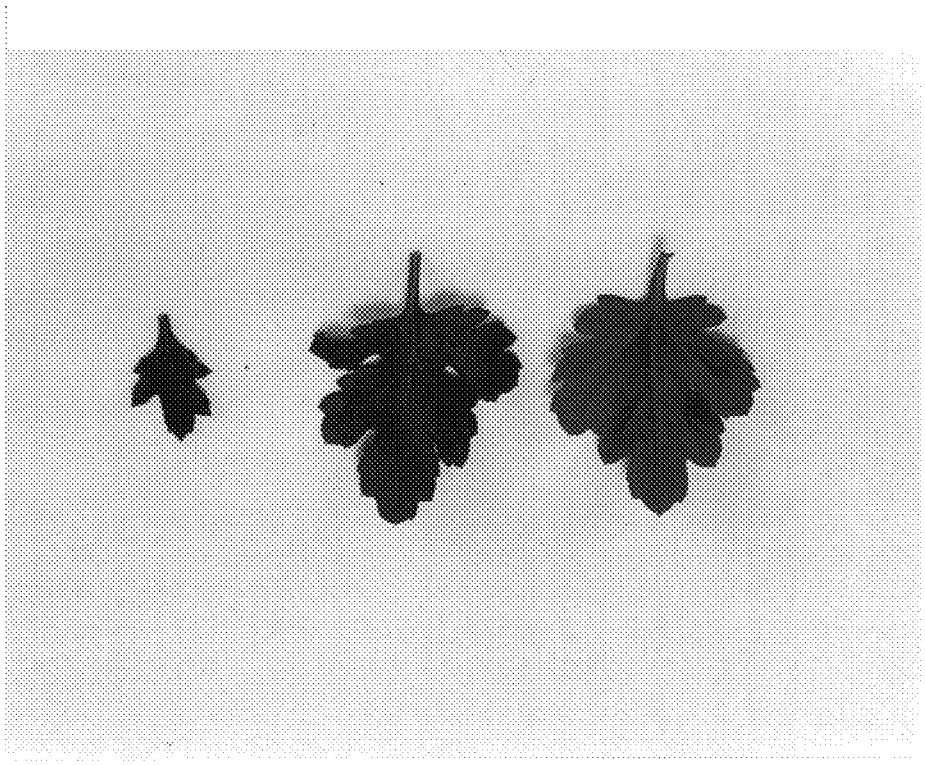
FIG. 3 shows the various stages of foliage of the new cultivar.

This new variety of chrysanthemum is of the botanical classification *Dendranthema grandiflora*. The observations and measurements were gathered from plants grown in a greenhouse in Rijsenhout, Holland in a photo-periodic controlled crop under conditions generally used in commercial practice. The photo-periodic response time in this crop was 48 days after an average of eight long days. This new variety produces medium sized blooms with salmon ray-florets and yellow-green disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'Everest Salmon' can be planted without assimilation lightning between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivars in comparison to 'Everest Salmon' are 'Everest Pink' and 'Everest White'. When 'Everest Pink', 'Everest Salmon' and 'Everest White' are being compared the following differences and similarities are noticed: The difference of 'Everest Pink', 'Everest Salmon' and 'Everest White' is the color of the ray-florets for which characteristics 'Everest Salmon' has been selected out of 'Everest Pink'. The color of the ray-florets of 'Everest Salmon' is salmon, the color of the ray-florets of 'Everest Pink' is pale pink, the color of the ray-florets of 'Everest White' is white. All other characteristics of 'Everest Pink' and 'Everest Salmon' are similar.

The following is a description of the plant and characteristics that distinguish 'Everest Salmon' as a new and distinct variety.

The color designations are taken from the plant itself. Accordingly, any discrepancies between the color designations and the colors depicted in the photographs are due to photographic tolerances.

| Botanical Description of CULTIVAR 'Everest Salmon' | | 'Everest Pink' | 'Everest White' |
|---|---|---|---|
| Bud | | | |
| Size | Small Cross-section ± 0.9 cm height ± 0.7 cm | | |
| Outside Color | Greyed-Orange 173 D | Purple 75 D | Yellow-Green 154 D |
| Involucral bracts | 2 rows, length 7 mm., width 2 mm. | | |
| Involucral bracts among disc-florets | Not present | | |
| Involucral bracts color | Green 138 B | | |
| Bloom | | | |
| Type | Daisy | | |
| Height | Flat | | |
| Size | Medium | | |
| Fully Expanded | 6.0–6.5 cm | | |
| Borne (number of blooms per branch) | Approx. 5 blooms per branch | | |
| Length of lateral branch | From top to bottom approx. 11.0 cm | | |
| Lateral branch, attachment | Medium | | |
| Branching | Good with 5 breaks after pinching | | |
| Performance on the plant | 5 weeks | | |
| Seeds | Not produced | | |
| Fragrance | Typical chrysanthemum | | |
| Color | | | |
| Center of the flower (disc-florets) | Immature Yellow-green 144 B mature Yellow-green 151 A | | |
| Color of upper surface of the majority of the ray-florets | Orange-Red 35 D and yellow 10 B at the base | Purple 75 B | White 155 A |
| Color of the lower surface of the majority of the ray-florets | Greyed-Orange 165 D | Purple 75 C | White 155 A |
| Tonality from Distance | A pot mum with salmon daisy flowers and a yellow-green disc | | |
| Discoloration to color | Red 36 C | To Purple 75 C | To White 155 D |
| Ray florets | | | |
| Texture | Upper and under side smooth | | |
| Number | 16–20 (1 row) | | |
| Cross-section | Concave | | |
| Longitudinal axis of majority | Reflexing | | |
| Margin | Entire | | |
| Length of corolla tube | Short | | |
| Ray floret length | 2.6–2.8 cm | | |
| Ray floret width | 0.8 cm | | |
| Ratio length/width | Medium | | |
| Shape of tip | Mamillate | | |
| Disc florets | | | |
| Disc diameter | Small (± 1.2 cm) | | |
| Distribution of disc florets | Numerous and clearly visible at all stages of flower head development | | |
| Type | Tubular | | |
| Color | Yellow-green 144 B | | |
| Receptacle shape | Conical raised | | |
| Reproductive Organs | | | |
| Stamen (present in disc florets | Yellow-green 144 A thin, 2 mm in length | | |
| Pollen | None | | |
| Styles (present in both ray and disc | Yellow-green 144 A thin | | |
| Style Length | 4 mm | | |
| Stigmas | Yellow-green 144 A | | |
| Stigma Width | 1 mm | | |
| Ovaries | Enclosed in calyx | | |
| Plant | | | |
| Form | A pot mum meant for indoor use | | |

-continued

| Botanical Description of CULTIVAR 'Everest Salmon' | | 'Everest Pink' | 'Everest White' |
|---|---|---|---|
| Growth habit | Upright | | |
| Growth rate | Moderate | | |
| Height | 18.0–21.0 cm | | |
| Width | Medium, 20.0–22.0 cm | | |
| Stem Color | Yellow-green 146 A | | |
| Stem Strength | Strong | | |
| Stem Brittleness | Present | | |
| Stem Anthocyanin Coloration | Present | | |
| Flowering Response (photo-periodic controlled crop, no natural growing) | 48 days | | |
| Foliage | | | |
| Color | Upper side yellow-green 147 A under side green 146 A | | |
| Size | Medium, length 6.5 cm, width 5.0 cm | | |
| Quantity (number per lateral branch) | 6–7 | | |
| Shape | Egg-shaped | | |
| Texture upper side | Fleshly | | |
| Texture under side | Smooth | | |
| Ribs and veins upper side | Ribs and veins well developed | | |
| Ribs and veins under side | Ribs and veins well developed | | |
| Edge | Crenated | | |
| Shape of Base of Sinus Between Lateral Lobes | Round | | |
| Margin of Sinus Between Lateral Lobes | Converging | | |
| Shape of Base | Cordate | | |
| Apex | Mucronate | | |
| Age | 56 days | | |

I claim:

1. A new and distinct variety of chrysanthemum plant as described and illustrated.

* * * * *